US00PP10100P

United States Patent [19]

Rother

[11] Patent Number: Plant 10,100

[45] Date of Patent: Nov. 4, 1997

[54] PETUNIA PLANT NAMED 'KILKENNY BELLS'

[76] Inventor: Reinhard W. Rother, 56 Emerald Monbulk Road, Emerald, Victoria 3782, Australia

[21] Appl. No.: 680,362

[22] Filed: Jul. 15, 1996

[51] Int. Cl.[6] ..... A01H 5/00

[52] U.S. Cl. ..... Plt./68.1

[58] Field of Search ..... Plt./68.1

*Primary Examiner*—James R. Feyrer

*Attorney, Agent, or Firm*—C. A. Whealy

[57] ABSTRACT

A distinct cultivar of Petunia plant named 'Kilkenny Bells', characterized by its large purple/violet flowers that face upwards; vigorous plant growth habit and rapid growth rate; spreading and decumbent plant habit; freely branching habit; large, elliptic and pubescent leaves; wide pedicels; and early flowering.

2 Drawing Sheets

The present invention relates to a new and distinct cultivar of Petunia plant, botanically known as *Petunia axillaris*, and hereinafter referred to by the cultivar name 'Kilkenny Bells'.

The new cultivar is a product of a planned breeding program conducted by the inventor in Emerald, Victoria, Australia. The objective of the breeding program was to create new Petunia cultivars having large flowers, a spreading plant habit, and desirable flower colors.

The new cultivar originated from a cross made by the inventor of the inventor's proprietary Petunia selection No. 492-X as the male or pollen parent with the inventor's proprietary Petunia selection No. 592-Y as the female or seed parent.

The cultivar Kilkenny Bells was discovered and selected by the inventor as a flowering plant within the progeny of the stated cross in a controlled environment in Emerald, Victoria, Australia. Asexual reproduction of the new cultivar by terminal cuttings taken at Emerald, Victoria, Australia, has shown that the unique features of this new Petunia are stable and reproduced true to type in successive generations.

The cultivar 'Kilkenny Bells' has not been observed under all possible environmental conditions. The phenotype may vary somewhat with variations in environment such as temperature and light intensity, without, however, any variance in genotype. The following observations, measurements and comparisons describe plants grown in Emerald, Victoria, Australia, under commercial production conditions.

The following traits have been repeatedly observed and are determined to be the unique characteristics of 'Kilkenny Bells'. These characteristics in combination distinguish 'Kilkenny Bells' as a new and distinct cultivar:

1. Large purple/violet flowers that face upwards.
2. Vigorous plant growth habit and rapid growth rate.
3. Spreading and decumbent plant habit.
4. Freely branching habit. Plants do not require pinching.
5. Large, elliptic and pubescent leaves.
6. Wide pedicels.
7. Early flowering.
8. Very floriferous with numerous flowers per plant.
9. Tolerant to rain, drought and temperature extremes.

The cultivar 'Kilkenny Bells' is most similar in flower color to the cultivar 'Pampas Fire' (disclosed in U.S. Plant Pat. No. 9,408). The cultivar differs from the cultivar 'Pampas Fire' in the following characteristics:

1. Plants of the cultivar 'Kilkenny Bells' are more compact than plants of the cultivar Pampas Fire.
2. Plants of the cultivar 'Kilkenny Bells' have elliptic leaves whereas plants of the cultivar 'Pampas Fire' have ovate leaves.

3. Leaves of plants of the cultivar 'Kilkenny Bells' are more pubescent than leaves of plants of the cultivar 'Pampas Fire'.
4. Flowers are larger on plants of the cultivar 'Kilkenny Bells' compared to plants of the cultivar 'Pampas Fire'.
5. Plants of the cultivar 'Kilkenny Bells' have spatulate sepals whereas plants of the cultivar 'Pampas Fire' have elliptic sepals.
6. The flower tube color and outside petal color is lighter on plants of the cultivar 'Kilkenny Bells' compared to plants of the cultivar 'Pampas Fire'.
7. Pedicels of plants of the cultivar 'Kilkenny Bells' are wider than plants of the cultivar 'Pampas Fire'.

A detailed comparison of the cultivars 'Kilkenny Bells' and 'Pampas Fire' appears in Chart A at the end of the specification.

The accompanying colored photographs illustrate the overall appearance of the new cultivar, showing the colors as true as it is reasonably possible to obtain in colored reproductions of this type.

The first photograph comprises a side perspective view of a typical hanging basket plant of the cultivar 'Kilkenny Bells'.The second photograph comprises a close-up view of individual flowers of the cultivar Kilkenny Bells.

Flower and foliage colors may appear different than the actual colors due to light reflectance.

In the following description, color references are made to The Royal Horticultural Society Colour Chart except where general terms of ordinary dictionary significance are used. Measurements are averages from ten specimens selected at random from five plants.

Botanical Classification: *Petunia axillaris* cultivar 'Kilkenny Bells'.

Parentage:

*Male or pollen parent.*—*Petunia axillaris*, inventor's proprietary selection No. 492-X.

*Female or seed parent.*—*Petunia axillaris*, inventor's proprietary selection No. 592-Y.

Propagation:

*Type cutting.*—Terminal vegetative cuttings.

*Time to initiate roots.*—About 10 days at 21C soil temperature.

*Rooting habit.*—Numerous, fine, fibrous, and well-branched.

Plant description:

*Form.*—Indeterminate, decumbent, diffuse spreading, viscid, glandular pubescent.

*Branching habit.*—Freely branching.

*Plant height.*—About 13.4 cm.

*Plant width.*—About 66.4 cm.

*Vigor.*—Vigorous.

*Crop time.*—8 to 9 weeks from a unrooted cutting to a 10.5-cm finished and flowering container.

*Foliage description.*—Leaves simple, generally symmetrical, sessile, and long persisting. Leaves at first whorled, later alternate, somewhat fleshy. Size (largest leaves): Length: About 11 cm. Width: About 4 cm. Thickness: About 2 mm. Shape: Elliptic. Aspect: Horizontal to upward. Apex: Obtuse. Base: Attenuate. Margin: Entire. Texture: Very pubescent. Color: Young foliage upper side: 137A. Young foliage under side: 147B. Mature foliage upper side: 137A. Mature foliage under side: 147B.

*Stem description.*—Stems spreading or hanging a length of at least one meter, hirsute. Stem diameter: About 3 mm. Internode length: About 2.9 cm. Stem color: Green, 144A, with purple tint.

Flower description:

*Flower type and habit.*—Large, single, salverform flowers, facing upwards, axillary. Calyx five-parted, petals united into a flower tube.

*Natural flowering season.*—Long day responsive, continuously flowers from spring through fall in Northern Hemisphere.

*Quantity.*—Numerous flowers per plant.

*Corolla.*—Diameter: About 8.2 cm. Height: About 6.5 cm. Flower tube width at distal end: Broad, about 1.8 cm. Petal quantity: Five, fused. Petal apex: Obtuse. Margin: Entire. Texture: Pubescent on outside, smooth and satiny on inside. Color: Flower throat (inside): 90C/90D. Flower throat vein color (inside): 83A. Flower tube color (outside): 87A. Flower tube vein color (outside): 144A. Petal color, inside: 78A. Petal color, outside: 85A. Petal vein color, outside: Yellow green.

*Sepals.*—Quantity: Five. Size: Length: About 3 cm. Width: About 8 mm. Shape: Spatulate. Apex: Obtuse. Margin: Entire. Texture: Pubescent. Aspect: Upright. Color: Inside: 137A. Outside: 137C.

*Pedicel.*—Aspect: Curved upright. Size: Length: About 2.3 cm. Width: About 2.4 mm. Texture: Pubescent. Color: 144A.

*Reproductive organs.*—Stigma level with anthers, superior ovary. Stamens: Stamen number: Five, four are didymous. Anther color: Blue. Filament color: Green white. Pistils: Stigma color: Green. Style color: Yellow green.

Disease resistance: No known Petunia diseases observed to date.

Fruit and seed production: Rarely observed.

*Fruit.*—Capsule with two undivided valves.

*Seeds.*—Minute, spherical.

CHART A

| CHARACTERISTIC | 'KILKENNY BELL' | 'PAMPAS FIRE' |
|---|---|---|
| LEAF LENGTH | 11 cm | 9.6 cm |
| LEAF WIDTH | 4 cm | 4.5 cm |
| LFAF SHAPE | Elliptic | Ovate |
| LEAF PUBESCENCE | Pubescent | Slightly pubescence |
| COROLLA DIAMETER | 8.2 cm | 7.6 cm |
| FLOWER TUBE WIDTH | 1.8 cm | 1.6 cm |
| SEPAL SHAPE | Spatulate | Elliptic |
| FLOWER THROAT COLOR | 90C/90D | 83A |
| FLOWER TUBE COLOR | 87A | 83A |
| FLOWER TUBE VEIN COLOR | Yellow green | Purple |
| PETAL COLOR, INSIDE | 78A | Darker than 74A |
| PETAL COLOR, OUTSIDE | 85A | 80C |
| PETAL VEIN COLOR, OUTSIDE | Yellow green | Purple |
| PEDICEL WIDTH | 2.4 mm | 1.6 mm |
| ANTHER COLOR | Blue | Violet |
| FILAMENT COLOR | Green white | Green white, violet tinge |

It is claimed:

1. A new and distinct cultivar of Petunia plant named 'Kilkenny Bells', as illustrated and described.

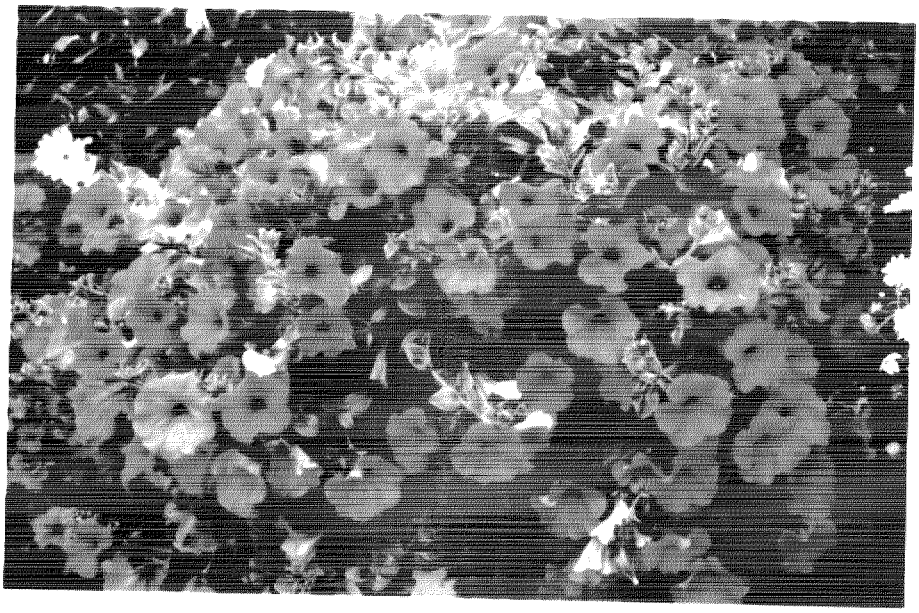

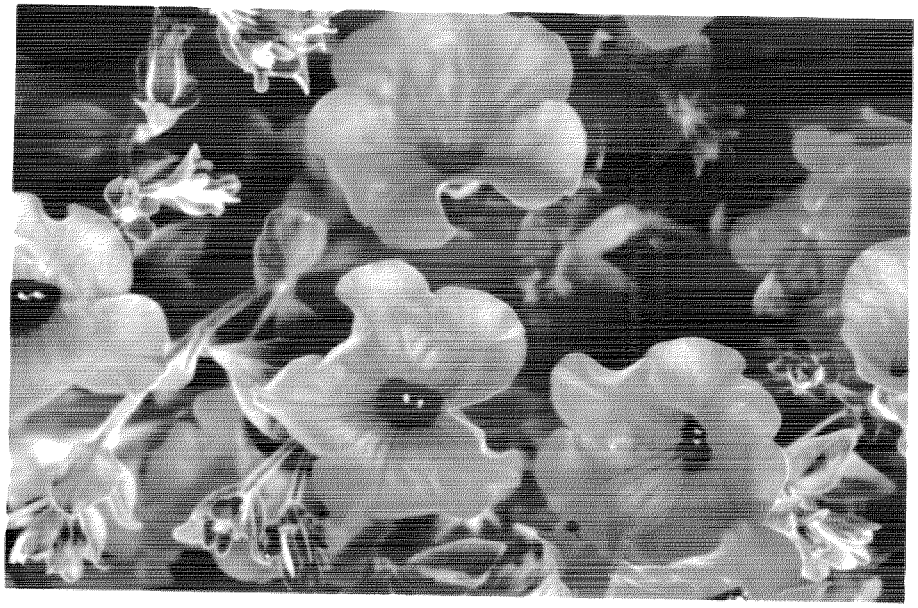

* * * * *